(12) United States Patent
Bohlmann et al.

(10) Patent No.: US 8,445,469 B2
(45) Date of Patent: May 21, 2013

(54) 18-METHYL-19-NOR-17-PREGN-4-ENE-21,17-CARBOLACTONES, AS WELL AS PHARMACEUTICAL PREPARATIONS THAT CONTAIN THE LATTER

(75) Inventors: Rolf Bohlmann, Berlin (DE); Dieter Bittler, Berlin (DE); Hermann Kuenzer, Berlin (DE); Peter Esperling, Berlin (DE); Hans-Peter Muhn, Berlin (DE); Karl-Heinrich Fritzemeier, Berlin (DE); Ulrike Fuhrmann, Berlin (DE); Katja Prelle, Berlin (DE); Steffen Borden, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 152 days.

(21) Appl. No.: 11/321,449

(22) Filed: Dec. 30, 2005

(65) Prior Publication Data

US 2006/0252737 A1    Nov. 9, 2006

Related U.S. Application Data

(60) Provisional application No. 60/640,065, filed on Dec. 30, 2004.

(30) Foreign Application Priority Data

Dec. 30, 2004   (DE) .......................... 10 2004 063 864

(51) Int. Cl.
*A61K 31/58*       (2006.01)
*C07J 21/00*       (2006.01)

(52) U.S. Cl.
USPC ........................................... 514/173; 540/41

(58) Field of Classification Search
USPC ........................................... 540/41; 514/173
See application file for complete search history.

(56) References Cited

U.S. PATENT DOCUMENTS

| | | | | |
|---|---|---|---|---|
| 3,455,909 A | * | 7/1969 | Smith et al. | 540/28 |
| 4,584,288 A | | 4/1986 | Nickish et al. | |
| 5,182,381 A | * | 1/1993 | Philibert et al. | 540/4 |
| 6,147,066 A | * | 11/2000 | Petit et al. | 514/178 |
| 6,177,416 B1 | * | 1/2001 | Laurent et al. | 514/175 |
| 6,864,248 B2 | * | 3/2005 | Cook et al. | 514/179 |
| 6,900,193 B1 | * | 5/2005 | Kim et al. | 514/179 |

OTHER PUBLICATIONS

Nickisch et al., J. Med. Chem., vol. 34, pp. 2464-2468, 1991.*
Kandemirli et al., II Farmaco, vol. 57, pp. 601-607, 2002.*
Nickisch et al., "Aldosterone Antagonists. 4. Synthesis and Activities of Steroidal 6,6-Ethylene-15,16-methylene 17-Spirolactones," J. Med. Chem., 1991, vol. 34, pp. 2464-2468.

* cited by examiner

*Primary Examiner* — Barbara P Badio
(74) *Attorney, Agent, or Firm* — Millen, White, Zelano & Branigan, P.C.

(57) ABSTRACT

A 18-Methyl-19-nor-17-pregn-4-ene-21,17-carbolactone of general formula I

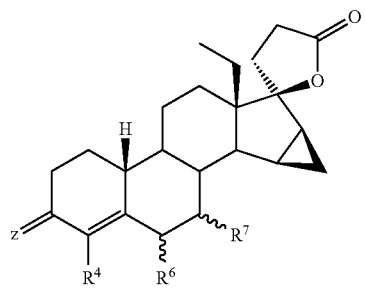

Formula I in which $Z, R^4, R^6, R^7$ are as defined below with the proviso that the compound is not 18-Methyl-15β,16β-methylene-3-oxo-19-nor-17-pregn-4-ene-21,17-carbolactone.

20 Claims, No Drawings

18-METHYL-19-NOR-17-PREGN-4-ENE-21,17-CARBOLACTONES, AS WELL AS PHARMACEUTICAL PREPARATIONS THAT CONTAIN THE LATTER

This application claims the benefit of the filing date of U.S. Provisional Application Ser. No. 60/640,065 filed Dec. 30, 2004, which is incorporated by reference herein This invention relates to 18-methyl-19-nor-17-pregn-4-ene-21,17-carbolactones of general formula I

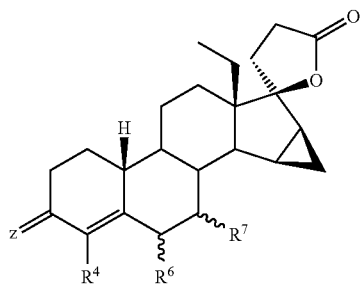

Formula I in which
  Z means an oxygen atom, two hydrogen atoms, a grouping =NOR or =NNHSO$_2$R, whereby R is a hydrogen atom or a straight-chain or branched-chain alkyl group with 1 to 4 or 3 to 4 carbon atoms,
  $R^4$ is a hydrogen atom, a halogen atom, a methyl group, or a trifluoromethyl group,
  $R^6$ and/or $R^7$ can be in α- or β-position, and, independently of one another, mean a straight-chain or branched-chain alkyl group with 1 to 4 or 3 to 4 carbon atoms, or
  $R^6$ means a hydrogen atom and $R^7$ means an α- or β-position, straight-chain or branched-chain alkyl group with 1 to 4 or 3 to 4 carbon atoms, or
  $R^6$ and $R^7$ each mean a hydrogen atom or
  $R^6$ and $R^7$ together mean α- or β-position methylene group or an additional bond.
  Z preferably stands for an oxygen atom.
  If Z stands for a grouping =NOR or =NNHSO$_2$R, R preferably is a hydrogen atom.
  A methyl, ethyl, n-propyl or n-butyl group or an isopropyl, iso- or tert-butyl group can be considered for a straight-chain or branched-chain alkyl group with 1 to 4 or 3 to 4 carbon atoms.
  $R^4$ is preferably a hydrogen atom.
  As halogen atom $R^4$, a fluorine, chlorine, bromine or iodine atom is suitable; chlorine is preferred among the latter.
  If $R^6$ and/or $R^7$ is a straight-chain or branched-chain alkyl group with 1 to 4 or 3 to 4 carbon atoms, a methyl, ethyl, n-propyl or n-butyl group or an isopropyl, iso- or tert-butyl group is considered in this respect.
  $R^6$ and $R^7$ preferably stand for a hydrogen atom and a methyl group or together for a methylene group or a double bond.
  Compounds that are mentioned below are especially preferred according to the invention:
  18-Methyl-15β,16β-methylene-3-oxo-19-nor-17-pregna-4,6-diene-21,17-carbolactone
  18-Methyl-6α,7α-15β,16β-dimethylene-3-oxo-19-nor-17-pregn-4-ene-21,17-carbolactone
  18-Methyl-6β,7β-15β,16β-dimethylene-3-oxo-19-nor-17-pregn-4-ene-21,17-carbolactone
  7α,18-Dimethyl-15β,16β-methylene-3-oxo-19-nor-17-pregn-4-ene-21,17-carbolactone
  7β,18-Dimethyl-15β,16β-methylene-3-oxo-19-nor-17-pregn-4-ene-21,17-carbolactone
  3-Hydroxylamino-18-methyl-6β,7β-15β,16β-dimethylene-19-nor-17-pregn-4-ene-21,17-carbolactone
  4-Chloro-18-methyl-6β,7β-15β,16β-dimethylene-3-oxo-19-nor-17-pregn-4-ene-21,17-carbolactone
  7α-Ethyl-18-methyl-15β,16β-methylene-3-oxo-19-nor-17-pregn-4-ene-21,17-carbolactone
  7β-Ethyl-18-methyl-15β,16β-methylene-3-oxo-19-nor-17-pregn-4-ene-21,17-carbolactone
  18-Methyl-15β,16β-methylene-3-oxo-7α-propyl-19-nor-17-pregn-4-ene-21,17-carbolactone
  18-Methyl-15β,16β-methylene-3-oxo-7β-propyl-19-nor-17-pregn-4-ene-21,17-carbolactone.

Drospirenone (6β,7β-15β,16β-dimethylene-3-oxo-17-pregn-4-ene-21,17β-carbolactone) is a new gestagen, which is contained in, for example, the oral contraceptive YASMIN® and the preparation ANGELIQ® for treating postmenopausal symptoms (both SCHERING AG). Based on its comparatively low affinity to the gestagen receptor and its comparatively high ovulation-inhibiting dose,

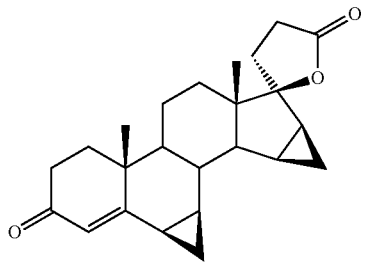

Drospirenone drospirenone in YASMIN® is contained in the relatively high daily dose of 3 mg. Drospirenone is characterized in that in addition to the gestagenic action, it has aldosterone-antagonistic (anti-mineralocorticoid) as well as antiandrogenic action. These two properties make the drospirenone very similar in its pharmacological profile to the natural gestagen progesterone, which, however, unlike drospirenone, is not sufficiently orally bio-available.

It is therefore the object of this invention to make available compounds that have a stronger bond to the gestagen receptor than the drospirenone and thus are to have a higher gestagenic power than the drospirenone. This is ultimately to be displayed in a lower daily dosage and is to result in a lower substance demand in the active compound.

This object is achieved by the preparation of the 18-methyl-19-nor-17-pregn-4-ene-21,17-carbolactones of general formula I that are described here. The compounds of general formula I (and in particular compound 3b, see experimental part) can be regarded as the constitutional isomers of the drospirenone. The new compounds are distinguished in the gestagen binding test with use of cytosol from the rabbit uterus homogenate and 3H-progesterone as a reference substance through a higher affinity to the gestagen receptor than drospirenone and through comparable affinity to the mineralocorticoid receptor from the rat kidney homogenate.

The binding to the gestagen receptor is in this case, surprisingly enough, up to 5× as strong as that of the drospirenone.

The compounds according to the invention are distinguished, surprisingly enough, by strong gestagenic action and are greatly effective in the pregnancy-maintenance test in rats after subcutaneous administration.

Executing the Pregnancy Maintenance Test in Rats:

In pregnant rats, removal of the corpora lutea or castration induces abortion. By exogenous supplying of progestins (gestagens) in combination with a suitable dose of estrogens, pregnancy can be maintained. The pregnancy maintenance test in ovariectomized rats serves to determine peripheral gestagenic activity of a compound.

Rats are paired up during the proestrus overnight. Mating is monitored on the morning of the following day by vaginal smear inspection. The presence of sperm is considered in this case as day 1 of the beginning of pregnancy. On day 8 of pregnancy, the animals are ovariectomized under ether anesthesia. Treatment with the test compound and exogenous estrogen (estrone, 5 µg/kg/day) is performed subcutaneously once daily on day 8 to day 15 or day 21 of pregnancy. The first administration on day 8 is performed 2 hours prior to castration. Intact control animals receive only the vehicle.

Evaluation:

At the end of the test (day 15 or day 21), the animals are sacrificed under $CO_2$ atmosphere, and live fetuses (fetuses with beating hearts) and implantation sites (early resorptions and dead fetuses including autolysis and atrophic placentas) in both uterine horns are counted. In addition, on day 22, fetuses can be inspected for malformations. In uteri without fetuses or implantation sites, the number of nidation sites is determined by staining with 10% ammonium sulfide solution. The pregnancy maintenance rate is calculated as the quotient of the number of living fetuses and the total number of nidation sites (both resorbed and dead fetuses as well as nidation sites). In this case, for the test substance 18-methyl-6α,7α-15β,16β-dimethylene-3-oxo-19-nor-17-pregn-4-ene-21,17-carbolactone (compound 3a, see the experimental section), a pregnancy-maintaining dose ($ED_{50}$) of 120 µg/kg/day was determined. For drospirenone, this value is 3.5 mg/kg/day.

The compounds of general formula I according to the invention have very strong gestagenic action with a simultaneously weaker binding to the androgen receptor (dissociation).

In addition, it was found that compounds according to the invention show a potassium-retaining, natriuretic (anti-mineralocorticoid) action in adrenalectomized rats.

Based on their gestagenic action, the new compounds of general formula I can be used by themselves or in combination with estrogen in pharmaceutical preparations for contraception.

Because of their advantageous profile of action, the compounds according to the invention are especially well suited for treatment of premenstrual symptoms, such as headaches, depressive mood disorders, water retention and mastodynia.

The dosage of the compounds according to the invention in contraceptive preparations is to be 0.01 to 5 mg, preferably 0.01 to 2 mg per day.

The daily dose in the treatment of premenstrual symptoms is approximately 0.1 to 20 mg.

The gestagenic and estrogenic active ingredient components are preferably administered orally together in contraceptive preparations. The daily dose is preferably administered once.

As estrogens, synthetic estrogens, preferably ethinyl estradiol, but also mestranol, are considered.

The estrogen is administered in a daily amount that corresponds to that of 0.01 to 0.04 mg of ethinyl estradiol.

The new compounds of general formula I can also be used in pharmaceutical preparations for treating pre-, peri- and post-menopausal symptoms, as well as in preparations for hormone substitution therapy (HRT).

As estrogens in such preparations, primarily natural estrogens, mainly estradiol or its esters, for example estradiol valerate or else conjugated estrogens (CEEs=conjugated equine estrogens), as they are contained in, for example, the preparation PREMARIN®, are used.

The formulation of the pharmaceutical preparations based on the new compounds is carried out in a way that is known in the art by the active ingredient, optionally in combination with an estrogen, being processed with the vehicles, diluents, optionally flavoring correctives, etc., that are commonly used in galenicals and being converted into the desired form of administration.

For the preferred oral administration, in particular tablets, coated tablets, capsules, pills, suspensions or solutions are suitable.

For parenteral administration, in particular oily solutions, such as, for example, solutions in sesame oil, castor oil and cottonseed oil, are suitable. To increase the solubility, solubilizers, such as, for example, benzyl benzoate or benzyl alcohol, can be added.

It is also possible to incorporate the substances according to the invention into a transdermal system and thus to administer them transdermally.

The new compounds of general formula I are produced as described below according to the invention. The synthesis route for the novel 18-methyl-6,7-15,16-dimethylene-3-oxo-19-nor-17-pregn-4-ene-21,17-carbolactones according to Diagram 1 starts in the example of compound 1 (DE 3402329).

The introduction of a $\Delta^6$-double bond is carried out with, for example, bromination of 3,5-dienamine or by a modified dienol ether bromination as well as subsequent hydrogen bromide cleavage (see, e.g., J. Fried, J. A. Edwards, *Organic Reactions in Steroid Chemistry*, von Nostrand Reinhold Company 1972, pp. 265-374).

Diagram 1

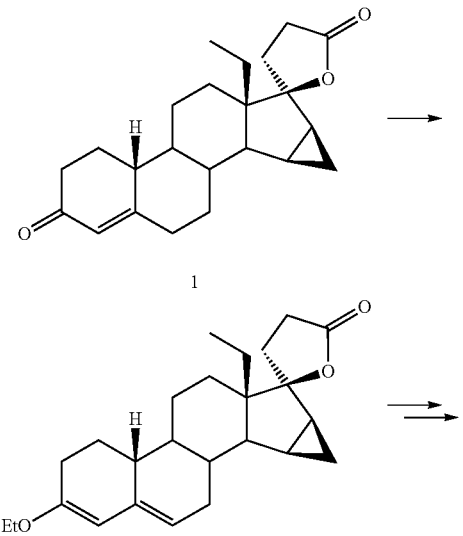

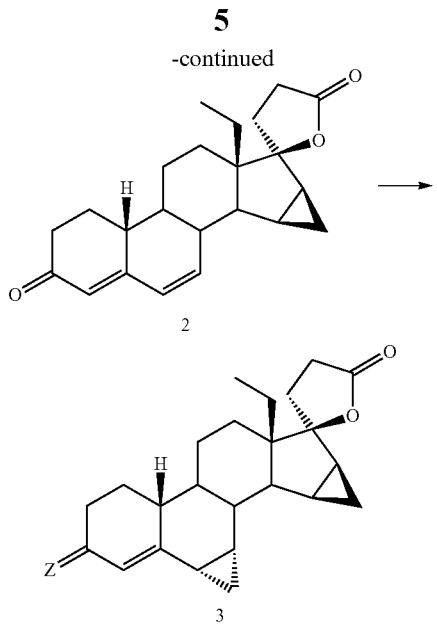

The dienol ether bromination can be carried out, e.g., analogously to the instructions of J. A. Zderic, Humberto Carpio, A. Bowers and Carl Djerassi in Steroids 1, 233 (1963). The hydrogen bromide cleavage can be accomplished by heating the 6-bromine compound with basic reagents, such as, e.g., LiBr or $Li_2CO_3$, in aprotic solvents, such as dimethylformamide, at temperatures of 50-120° C. or else by the 6-bromine compounds in a solvent such as collidine or lutidine being heated to compound 2 (Example 1).

Compound 2 is then converted into a compound 3 by methylenation of the $\Delta^6$-double bond according to known processes, e.g., with dimethyl sulfoxonium methylide (see, e.g., DE-A 11 83 500, DE-A 29 22 500, EP-A 0 019 690, U.S. Pat. No. 4,291,029; E. J. Corey and M. Chaykovsky, *J. Am. Chem. Soc.* 84, 867 (1962)), whereby a mixture of α- and β-isomers (compounds 3a/3b) is obtained (the ratio is dependent on the substrates used and is approximately 1:1), which can be separated into the individual isomers by, e.g., chromatography.

The introduction of a substituent $R^4$ can be handled, for example, starting from a compound of formula 3 by epoxidation of the $\Delta^4$-double bond with hydrogen peroxide under alkaline conditions and reaction of the epoxides that are produced in a suitable solvent with acids of general formula H—$R^4$, whereby —$R^4$ can be a halogen atom or a pseudohalogen, or is reacted with catalytic amounts of mineral acid, and optionally the 4-bromine compounds of general formula I that are obtained (whereby $R^4$=bromine) are reacted with 2,2-difluoro-2-(fluorosulfonyl)acetic acid methyl ester in dimethylformamide in the presence of copper (I) iodide.

The introduction of a 6-methylene group can be carried out, for example, starting from a 3-amino-3,5-diene derivative by reaction with formalin in alcoholic solution with the formation of a 6α-hydroxymethyl group and subsequent acidic dehydration with, e.g., hydrochloric acid in dioxane/water. The dehydration, however, can also be carried out in the way that first the hydroxy group is exchanged for a better leaving group and then eliminated. As leaving groups, e.g., the mesylate, tosylate or benzoate is suitable (see DE-A 34 02 3291, EP-A. 0 150 157, U.S. Pat. No. 4,584,288; K. Nickisch et al., *J. Med. Chem.* 34, 2464 (1991)).

Another possibility for the production of 6-methylene compounds exists in the direct reaction of 4(5)-unsaturated 3-ketones with acetalene of the formaldehyde in the presence of sodium acetate with, e.g., phosphorus oxychloride or phosphorus pentachloride in suitable solvents such as chloroform (see, e.g., K. Annen, H. Hofmeister, H. Laurent and R. Wiechert, *Synthesis* 34 (1982)).

The 6-methylene compounds can be used for the production of compounds of general formula I, in which $R^6$ is equal to methyl, and $R^6$ and $R^7$ together form an additional bond.

To this end, there can be used, e.g., a process that is described by D. Burn et al. in *Tetrahedron* 21, 1619 (1965) in which an isomerization of the double bond can be achieved by heating the 6-methylene compounds in ethanol with 5% palladium-carbon catalyst, which was pretreated either with hydrogen or by heating with a small amount of cyclohexene. The isomerization can also be carried out with a non-pretreated catalyst, if a small amount of cyclohexene is added to the reaction mixture. The occurrence of small proportions of hydrogenated products can be prevented by adding excess sodium acetate.

The production of 6-methyl-4,6-dien-3-one derivatives can also be carried out directly, however (see K. Annen, H. Hofmeister, H. Laurent and R. Wiechert, *Lieb. Ann.* 712 (1983)).

Compounds in which $R^6$ represents an α-methyl function can be produced from the 6-methylene compounds by hydrogenation under suitable conditions. The best results (selective hydrogenation of the exo-methylene function) are achieved by transfer hydrogenation (E. A. Brande, R. P. Linstead and P. W. D. Mitchell, *J. Chem. Soc.* 3578 (1954)). If the 6-methylene derivatives are heated in a suitable solvent, such as, e.g., ethanol, in the presence of a hydride donor, such as, e.g., cyclohexene, very good yields of 6α-methyl derivatives thus result. Small portions of 6β-methyl compound can be isomerized in acidic form (see, e.g., D. Burn, D. N. Kirk and V. Petrow, *Tetrahedron* 1619 (1965)).

The specific production of 6β-alkyl compounds is also possible. In this respect, the 4(5)-unsaturated 3-ketones are reacted with, e.g., ethylene glycol, trimethyl orthoformate in dichloromethane in the presence of catalytic amounts of an acid (e.g., p-toluenesulfonic acid) to form the corresponding 3-ketals. During this ketalization, the double bond isomerizes in 5(6)-position. A selective epoxidation of this 5(6)-double bond can be accomplished by, e.g., using organic peracids, e.g., m-chloroperbenzoic acid, in suitable solvents such as dichloromethane. As an alternative to this, the epoxidation can also be carried out with hydrogen peroxide in the presence of, e.g., hexachloroacetone or 3-nitrotrifluoroacetophenone. The 5,6α-epoxides that are formed can then be opened axially with use of corresponding alkylmagnesium halides or alkyl lithium compounds. 5α-Hydroxy-6β-alkyl compounds are thus obtained. The cleavage of the 3-keto protective group can be carried out while obtaining the 5α-hydroxy function by treatment under mild acidic conditions (acetic acid or 4N hydrochloric acid at 0° C.). Basic elimination of the 5α-hydroxy function with, e.g., dilute aqueous sodium hydroxide solution yields the 3-keto-4-ene compounds with a β-position 6-alkyl group. As an alternative to this, the ketal cleavage under more drastic conditions (aqueous hydrochloric acid or another strong acid) yields the corresponding 6α-alkyl compounds.

The compounds of general formula I that are obtained, in which Z stands for an oxygen atom, can optionally be converted by reaction with hydroxylamine hydrochloride in the presence of a tertiary amine at temperatures of between −20 and +40° C. into their corresponding oximes (general formula I with Z in the meaning of =NOH, whereby the hydroxy group can be in syn- or anti-position). Suitable tertiary bases are, for example, trimethylamine, triethylamine, pyridine, N,N-dimethylaminopyridine, 1,5-diazabicyclo[4.3.0]non-5-ene (DBN) and 1,5-diazabicyclo[5.4.0]undec-5-ene (DBU), whereby pyridine is preferred. This is analogous to the description in WO 98/24801 for the production of corresponding 3-oxyimino derivatives of the drospirenone.

The removal of the 3-oxo group for the production of an end product of general formula I with Z in the meaning of two hydrogen atoms can be carried out, for example, according to the instructions that are indicated in DE-A 28 05 490 by reductive cleavage of a thioketal of the 3-keto compound.

The examples below are used for a more detailed explanation of the invention:

EXAMPLE 1

18-Methyl-15β,16β-methylene-3-oxo-19-nor-17-pregna-4,6-diene-21,17-carbolactone 11 ml of o-formic acid triethyl ester as well as 11 ml of dioxane/sulfuric acid (12+0.42) are added to a solution of 11.0 g of 18-methyl-15β,16β-methylene-3-oxo-19-nor-17-pregn-4-ene-21,17-carbolactone (DE3402329) in 110 ml of dioxane. 14.4 g of 3-ethoxy-18-methyl-15β,16β-methylene-19-nor-17-pregna-3,5-diene-21,17-carbolactone was obtained as a crude product. The latter was dissolved in 380 ml of acetone, mixed with 2.3 ml of pyridine, 10.3 g of sodium acetate, 28 ml of water as well as 7.6 g of N-bromosuccinimide, and it was stirred for 0.5 hour at ice bath temperature. Then, it was stirred into ice water, the precipitate was filtered out, it was washed with water, the precipitate was taken up in dichloromethane, washed with water, dried on sodium sulfate and concentrated by evaporation in a vacuum. 17 g of 6-bromo-18-methyl-3-oxo-15β,16β-methylene-19-nor-17-pregn-4-ene-21,17-carbolactone was obtained as a crude product. The latter was dissolved in 170 ml of dimethylformamide and stirred with 6.65 g of lithium bromide as well as 7.87 g of lithium carbonate for one hour at 100° C. Then, it was stirred into ice water, the precipitate was filtered out, washed with water, the precipitate was taken up in dichloromethane, washed with water, dried on sodium sulfate and concentrated by evaporation in a vacuum. After chromatography on silica gel with hexane/acetone, 6.5 g of 18-methyl-15β,16β-methylene-3-oxo-19-nor-17-pregna-4,6-diene-21,17-carbolactone (compound 2 in Diagram 1) with a melting point of 187° C. is obtained.

EXAMPLE 2

18-Methyl-6α,7α-15β,16β-dimethylene-3-oxo-19-nor-17-pregn-4-ene-21,17-carbolactone A solution of 5.8 g of 18-methyl-15β,16β-methylene-3-oxo-19-nor-17-pregna-4,6-diene-21,17-carbolactone in 200 ml of dimethyl sulfoxide was mixed with 9.06 g of trimethylsulfoxonium iodide and 1.613 g of sodium hydride (55% suspension in oil), and it was stirred for 20 hours under argon at room temperature. Then, it was stirred into ice water, turned weakly acidic, the precipitate was filtered out, the precipitate was taken up in dichloromethane, washed with water, dried on sodium sulfate, concentrated by evaporation in a vacuum, and chromatographed on silica gel with hexane/acetone. After recrystallization of fraction III from 2-propanol/acetone, 0.8 g of 18-methyl-6α,7α-15β,16β-dimethylene-3-oxo-19-nor-17-pregn-4-ene-21,17-carbolactone (compound 3a) was obtained as crystals with a melting point of 262° C. $[\alpha]_D=+89.7°$ (methanol, c=10.15 mg/ml)

EXAMPLE 3

18-Methyl-6β,7β-15β,16β-dimethylene-3-oxo-19-nor-17-pregn-4-ene-21,17-carbolactone According to the method of Example 2, 0.9 g of 18-methyl-6β,7β-15β,16β-dimethylene-3-oxo-19-nor-17-pregn-4-ene-21,17-carbolactone (compound 3b) was obtained after the chromatography as fraction IV as a solid with a melting point of 189-190° C. $[\alpha]_D=-121.4°$ (chloroform, c=10.7 mg/ml) and $[\alpha]_D=+137.9°$ (methanol, c=10.63 mg/ml)

EXAMPLE 4

7α,18-Dimethyl-15β,16β-methylene-3-oxo-19-nor-17-pregn-4-ene-21,17-carbolactone

In a solution of 0.4 g of 18-methyl-15β,16β-methylene-3-oxo-19-nor-17-pregna-4,6-diene-21,17-carbolactone in 7 ml of tetrahydrofuran, 12 mg of copper(I) chloride was added at room temperature and stirred for 10 minutes before it was cooled to −15° C., mixed with 75 mg of aluminum chloride, stirred for 30 minutes at this temperature, mixed drop by drop with 0.8 ml of methylmagnesium bromide solution (3 M in diethyl ether), and stirred for one hour at −10° C. For working-up, the reaction mixture was mixed with 4N hydrochloric acid at −10° C., stirred for 1.5 hours at room temperature, added to water, extracted three times with ethyl acetate, dried on sodium sulfate, concentrated by evaporation in a vacuum and chromatographed on silica gel with hexane/ethyl acetate. After recrystallization of fraction I, 182 mg of 7α,18-dimethyl-15β,16β-methylene-3-oxo-19-nor-17-pregn-4-ene-21,17-carbolactone as crystals with a melting point of 250° C. was obtained. $[\alpha]_D=53.1+/-0.3°$ (chloroform, c=10.3 mg/ml)

EXAMPLE 5

7β,18-Dimethyl-15β,16β-methylene-3-oxo-19-nor-17-pregn-4-ene-21,17-carbolactone

According to the method of Example 4, after chromatography as fraction II, 36 mg of 7β,18-dimethyl-15β,16β-methylene-3-oxo-19-nor-17-pregn-4-ene-21,17-carbolactone was obtained as a solid with a melting point of 226° C. $[\alpha]_D=9.0+/-0.5°$ (chloroform, c=10.2 mg/ml).

EXAMPLE 6

7α-Ethyl-18-methyl-15β,16β-methylene-3-oxo-19-nor-17-pregn-4-ene-21,17-carbolactone 15 mg of copper(I) chloride was added at room temperature to a solution of 0.5 g of 18-methyl-15β,16β-methylene-3-oxo-19-nor-17-pregna-4,6-diene-21,17-carbolactone in 10 ml of tetrahydrofuran, and it was stirred for 10 minutes before it was cooled to −15° C., mixed with 93 mg of aluminum chloride, stirred for 30 minutes at this temperature, mixed drop by drop with 1.0 ml of ethyl magnesium bromide solution (3 M in diethyl ether), and stirred for one hour at −10° C. For working-up, the reaction mixture was mixed with 3 ml of 2N hydrochloric acid at −10° C., stirred for 0.5 hour at room temperature, poured into water, extracted three times with ethyl acetate, dried on sodium sulfate, concentrated by evaporation in a vacuum, and chromatographed on silica gel with hexane/ethyl acetate. After recrystallization of fraction I, 180 mg of 7α-ethyl-18-methyl-15β,16β-methylene-3-oxo-19-nor-17-pregn-4-ene-21,17-carbolactone was obtained as crystals with a melting point of 205-208° C. [α]$_D$=+34.4+/−0.3° (chloroform, c=10.3 mg/ml)

EXAMPLE 7

7β-Ethyl-18-methyl-15β,16β-methylene-3-oxo-19-nor-17-pregn-4-ene-21,17-carbolactone According to the method of Example 6, after chromatography as fraction II, 110 mg of 7β-ethyl-18-methyl-15β,16β-methylene-3-oxo-19-nor-17-pregn-4-ene-21,17-carbolactone was obtained as a solid with a melting point of 169-171° C. [α]$_D$=+30.8+/−0.5° (chloroform, c=10.1 mg/ml).

EXAMPLE 8

18-Methyl-15β,16β-methylene-3-oxo-7α-propyl-19-nor-17-pregn-4-ene-21,17-carbolactone 15 mg of copper(I) chloride was added at room temperature to a solution of 0.5 g of 18-methyl-15β,16β-methylene-3-oxo-19-nor-17-pregna-4,6-diene-21,17-carbolactone in 10 ml of tetrahydrofuran, and it was stirred for 10 minutes before it was cooled to −15° C., mixed with 93 mg of aluminum chloride, stirred for 30 minutes at this temperature, mixed drop by drop with 1.5 ml of propylmagnesium bromide solution (2 M in tetrahydrofuran) and stirred for one hour at −10° C. For working-up, the reaction mixture was mixed with 3 ml of 2N hydrochloric acid at −10° C., stirred for 0.5 hour at room temperature, poured into water, extracted three times with ethyl acetate, dried on sodium sulfate, concentrated by evaporation in a vacuum and chromatographed on silica gel with hexane/ethyl acetate. After recrystallization of fraction I, 177 mg of 18-methyl-15β,16β-methylene-3-oxo-7α-propyl-19-nor-17-pregn-4-ene-21,17-carbolactone was obtained as crystals with a melting point of 167.5° C. [α]$_D$=+31.2+/−0.3° (chloroform, c=10.1 mg/ml)

EXAMPLE 9

18-Methyl-15β,16β-methylene-3-oxo-7β-propyl-19-nor-17-pregn-4-ene-21,17-carbolactone According to the method of Example 8, after chromatography as fraction II, 105 mg of 18-methyl-15β,16β-methylene-3-oxo-7β-propyl-19-nor-17-pregn-4-ene-21,17-carbolactone was obtained as a solid with a melting point of 90.9° C. [α]$_D$=+27.4+/−0.4° (chloroform, c=10.3 mg/ml).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102004063864.0, filed Dec. 30, 2004, and U.S. Provisional Application Ser. No. 60/640,065, filed Dec. 30, 2004, are incorporated by reference herein. The disclosure from U.S. 60/640,065 includes that the invention relates to 18-methyl-19-nor-17-pregn-4-ene-21,17-carbolactones of general formula I

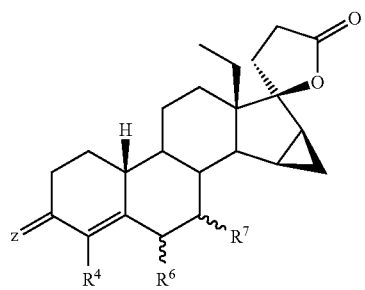

Formula I in which
Z means an oxygen atom, two hydrogen atoms, a grouping =NOR or =NNHSO$_2$R, whereby R is a hydrogen atom or a straight-chain or branched-chain alkyl group with 1 to 4 or 3 to 4 carbon atoms,
R$^4$ is a hydrogen atom, a halogen atom, or a trifluoromethyl group,
R$^6$ and/or R$^7$ can be in α- or β-position, and R$^6$ and R$^7$, independently of one another, mean a hydrogen atom or a straight-chain or branched-chain alkyl group with 1 to 4 or 3 to 4 carbon atoms or together a methylene group or a double bond.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A 18-Methyl-19-nor-17-pregn-4-ene-21,17-carbolactone of general formula I

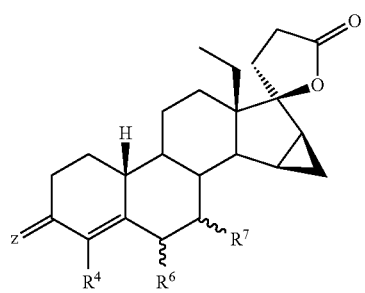

Formula I in which
Z means an oxygen atom,
R$^4$ is a hydrogen atom,
R$^6$ and R$^7$ can be in α- or β-position, and, independently of one another, mean a straight-chain or branched-chain alkyl group with 1 to 4 carbon atoms, or
R$^6$ means a hydrogen atom, and R$^7$ means an α- or β-position, straight-chain or branched-chain alkyl group with 1 to 4 carbon atoms, or
R$^6$ and R$^7$ each mean a hydrogen atom, or
R$^6$ and R$^7$ together mean an α- or β-position methylene group or an additional bond,
with the proviso that the compound is not 18-Methyl-15β,16β-methylene-3-oxo-19-nor-17-pregn-4-ene-21,17-carbolactone.

2. A compound of general formula I according to claim 1, in which $R^6$ stands for a hydrogen atom, and $R^7$ stands for a methyl group.

3. A compound of general formula I according to claim 1, in which $R^6$ stands for a hydrogen atom and $R^7$ stands for a propyl group.

4. A compound of general formula I according to claim 1, in which $R^6$ and $R^7$ together stand for a methylene group.

5. A compound of general formula I according to claim 1, in which $R^6$ and $R^7$ together stand for a double bond.

6. A compound of claim 1, wherein $R^6$ or $R^7$ is of 3-4 carbon atoms.

7. A compound of general formula I according to claim 1, in which $R^6$ and $R^7$ can be in α- or β-position, and, independently of one another, mean a straight-chain or branched-chain alkyl group with 1 to 4 carbon atoms.

8. A compound selected from the group consisting of
18-Methyl-15β,16β-methylene-3-oxo-19-nor-17-pregna-4,6-diene-21,17-carbolactone
18-Methyl-6α, 7α-15β,16β-dimethylene-3-oxo-19-nor-17-pregn-4-ene-21,17-carbolactone
18-Methyl-6β,7β-15β,16β-dimethylene-3-oxo-19-nor-17-pregn-4-ene-21,17-carbolactone
7α,18-Dimethyl-15β,16β-methylene-3-oxo-19-nor-17-pregn-4-ene-21,17-carbolactone
7β,18-Dimethyl-15β,16β-methylene-3-oxo-19-nor-17-pregn-4-ene-21,17-carbolactone
7α-Ethyl-18-methyl-15β,16β-methylene-3-oxo-19-nor-17-pregn-4-ene-21,17-carbolactone
7β-Ethyl-18-methyl-15β,16β-methylene-3-oxo-19-nor-17-pregn-4-ene-21,17-carbolactone
18-Methyl-15β,16β-methylene-3-oxo-7α-propyl-19-nor-17-pregn-4-ene-21,17-carbolactone and
18-Methyl-15β,16β-methylene-3-oxo-7β-propyl-19-nor-17-pregn-4-ene-21,17-carbolactone.

9. A 18-Methyl-19-nor-17-pregn-4-ene-21,17-carbolactone of general formula I

Formula I in which

Z means an oxygen atom, $R^4$ is a hydrogen atom, $R^6$ and/or $R^7$ can be in α- or β-position, and $R^6$ and $R^7$, independently of one another, mean a hydrogen atom or a straight-chain or branched-chain alkyl group with 1 to 4 carbon atoms or together a methylene group or a double bond, with the proviso that the compound is not 18-Methyl-15β, 16β-methylene-3-oxo-19-nor-17-pregn-4-ene-21,17-carbolactone.

10. A compound of general formula I according to claim 9, in which $R^6$ and $R^7$, independently of one another, mean a hydrogen atom or a straight-chain or branched-chain alkyl group with 1 to 4 carbon atoms.

11. A pharmaceutical preparation comprising at least one compound according to claim 1 and a pharmaceutically acceptable vehicle.

12. A pharmaceutical preparation according to claim 11, in addition containing at least one estrogen.

13. A pharmaceutical preparation according to claim 12, containing ethinyl estradiol.

14. A pharmaceutical preparation according to claim 12, containing a natural estrogen.

15. A pharmaceutical preparation according to claim 14, containing estradiol.

16. A pharmaceutical preparation according to claim 14, containing estradiol valerate.

17. A pharmaceutical preparation according to claim 14, containing at least one conjugated estrogen.

18. A method of hormone replacement therapy comprising administering to a subject in need thereof an effective amount of a compound of claim 1.

19. A method of contraception comprising administering to a subject in need thereof an effective amount of a preparation of claim 12.

20. A method of contraception or hormone replacement therapy comprising administering to a subject in need thereof an effective amount of a compound of claim 8, wherein in case of hormone replacement therapy an estrogen is also administered.

* * * * *